United States Patent [19]

Goepp

[11] 4,384,572
[45] May 24, 1983

[54] IMPLEMENT FOR MAKING AN IMPRESSION OF THE CERVIX UTERI

[75] Inventor: Robert A. Goepp, Chicago, Ill.

[73] Assignee: University Patents, Inc., Norwalk, Conn.

[21] Appl. No.: 236,772

[22] Filed: Feb. 23, 1981

Related U.S. Application Data

[63] Continuation-in-part of Ser. No. 108,319, Dec. 31, 1979, Pat. No. 4,322,463.

[51] Int. Cl.³ .......................... A61F 5/46; B29C 1/14
[52] U.S. Cl. .................................. 128/130; 264/222; 264/DIG. 30; 128/131
[58] Field of Search .............. 128/131, 127, 128, 130, 128/300, 281, 301, 302; 264/222, DIG. 30

[56] References Cited

U.S. PATENT DOCUMENTS

| | | | |
|---|---|---|---|
| 124,474 | 3/1872 | Banning, Jr. | 128/127 |
| 996,974 | 7/1911 | Chellis | 128/300 |
| 2,459,925 | 1/1949 | Curteman | 264/DIG. 30 |
| 4,007,249 | 2/1977 | Erb | 128/131 |

Primary Examiner—Kyle L. Howell
Assistant Examiner—Nancy A. B. Swisher

[57] ABSTRACT

An implement is provided for in situ molding of an impression of a cervix uteri from a medical grade impression paste. In the preferred form, the implement is an impression tray with a flexible cervix uteri-receiving cup and a hollow-elongated stem which is connected to the cup for passage of impression paste into the cup. The cup is fabricated with a circumferential flange that extends radially inwardly from the annular rim of the cup. The circumferential flange provides a retainer which holds the cervix uteri in place and also resiliently seals against the exocervical surface of the cervix uteri to facilitate retention of the impression paste in the cup during in situ molding of the cervical impression.

13 Claims, 12 Drawing Figures

IMPLEMENT FOR MAKING AN IMPRESSION OF THE CERVIX UTERI

CROSS-REFERENCE TO RELATED APPLICATIONS

This application is a continuation-in-part of the co-pending application of Robert A. Goepp and Uwe E. Freese, U.S. Ser. No. 108,319, filed Dec. 31, 1979, now U.S. Pat. No. 4,322,463, issued Mar. 30, 1982 for a custom valved cervical cap.

TECHNICAL FIELD

This invention relates to means for making contraceptive devices, and more particularly, to an implement for making an impression of a cervix uteri preparatory to molding a cervical cap.

BACKGROUND OF THE INVENTION

Caps for cervix uteri as a birth control means have been known for a long time and have been found among the artifacts of antiquity. It has been reported that Aetius of Amida suggested for this purpose the use of a pomegranate shell cut into a hollow cup, and that beeswax discs fashioned to fit over the cervix have been used in Europe.

Modern cervical caps comprise a pre-formed rubber cap that is positioned over the cervix uteri to act as a sperm barrier. Such caps are manufactured in several sizes to accommodate the various uterine sizes normally encountered; however, with such caps the fit for a particular individual is inexact and necessarily a compromise. As a result, these caps often become dislodged during coitus and have to be removed periodically to accommodate normal uterine discharges. Thus, such caps are inconvenient to use and have not achieved a high degree of reliability.

Typifying the many types of cervical caps that have been developed are those shown in U.S. Pat. Nos. 2,836,177 to Sells, 3,952,737 to Lipfert et al and 4,007,249 to Erb, German Pat. No. 475,496 to Leopold, as well as in *Das Weibliche Gebar-Unvermogen* by F. A. Wilde in Berlin in 1838 according to aforementioned U.S. Pat. No. 4,007,249. These cervical caps have met with varying degrees of success. In particular, the cap shown in U.S. Pat. No. 4,007,249 to Erb is said to be made while the vaginal wall is expanded by means of a speculum. Such an expedient tends to deform the cervix and thus precludes a good fit between the cap and the cervix because the attendant cervical distortion exceeds the limits of prosthetic stability of the produced cap. Additionally, medical grade silicone rubber, the material of choice in said patent for making the cap, is not readily wettable, thus surface tension cannot be relied upon to hold the cap properly in place on the cervix. In addition, some medical grade silicone rubbers are porous, and mucous uterine discharges and bacteria are likely to accummulate in the pores, thereby causing unpleasant odor, in addition to a risk of infection. In such instances, cervical caps may be usable only for a limited time period, e.g., about 6-8 hours.

The foregoing expedient is also impractical because the surface to which the liquid, polymerizable material is applied is wet with mucus and quite slippery, thus the applied material is likely to fall off the exocervical surface due to gravity before polymerization of the material could take place and, in any event, it would be impossible to control the thickness of the applied polymerizable material during in situ polymerization. A cervical cap having a relatively non-uniform thickness is undesirable, however, because it is unstable and is likely to be dislodged in use.

A further shortcoming of the caps shown in the Erb patent is that the prefabricated valving means utilized are of the leaflet or flap type. In such valves a viscous droplet of cervical mucus can hold the valve in an open position for an undesirably long time period, thereby providing an access aperture for sperm and defeating the very purpose of the cap. Moreover, inasmuch as the polymerizable material of the cap is in a fluid state when it surrounds the prefabricated valve, some of the fluid material may become enmeshed with the valve and interfere with its intended valving action after the material has polymerized.

U.S. Pat. No. 4,007,249 to Erb also briefly mentions a technique disclosed initially by F. A. Wilde in 1838 in *Das Weibliche-Gebar-Unvermogen* according to which a cervical cap allegedly can be made from a special wax impression of the vaginal portion of the cervix. As recognized by Erb, such a technique cannot produce an identical, negative-image, cervix-conforming inside surface because the cervix would be deformed while the wax impression is being made. The uterus is suspended in the lower abdomen by ligaments, is easily movable, and would tend to move up into the abdomen even with a gentle force applied to the cervix. As a result, accurate registration would be prevented by such a movement with attendant lack of stability for the cervical cap produced in such manner.

The techniques described by Erb are also likely to suffer from the same drawback, albeit for a different reason. In particular, in practicing these techniques the vaginal wall has to be expanded using a vaginal speculum or similar implement in order to expose the cervix during cap molding. This expedient tends to distort the cervix as well, elongating it along an imaginary line between the tips of the inserted, open vaginal speculum blades and shortening the cervix along an imaginary line at right angles to the imaginary line between the tips of the speculum blades. The attendant cervical distortion exceeds the limits for prosthetic stability of the cervical cap that is produced.

SUMMARY OF THE INVENTION

The present invention pertains to making a non-invasive birth control device in the form of a removable cervical cap. To this end an implement is provided for in situ molding of an impression of a cervix uteri from a medical grade impression paste, such as sodium alginate paste. Preferably the implement is used together with an impression-paste dispensing syringe.

The implement embodying the present invention includes an impression tray with a flexible cervix uteri-receiving cap and a hollow, elongated stem which is connected to the cup for introducing impression paste into the cup's interior. The cervix uteri-receiving cap has a resilient circumferential flange that extends radially inwardly from the rim of the cup. The circumferential flange traps and positions the cervix uteri, minimizing the tendency for the upwardly rotation of the cervix while the female patient is in supine position as the cervical impression is made. The flange also provides a retainer which resiliently seals against the exocervical surface of the cervix uteri and facilitates retention of the impression paste in the cup during the in situ molding of the cervical impression.

The inwardly extending flange is resilient and has a width that is substantially less than the radius of the aperture defined by the rim of the cup, usually about one-fifth (1/5) of the rim aperture radius. Thickness of the flange preferably is less than the thickness of the cup wall. More preferably, the flange thickness is about 0.8 to about 1.2 millimeters.

In a preferred form the cup is bell-shaped having an outwardly flared rim defining a mouth from which the flange extends inwardly and a bottom wall from which a sleeve depends. The sleeve receives one end of the aforesaid hollow, elongated stem and preferably is flexibly joined to the cup. The flexible sleeve and the stem received therein extend along a longitudinal axis which intersects the longitudinal axis of the cup at an included angle of about 15 degrees to about 25 degrees, and more preferably at about 20 degrees. Preferably, the cup is also provided with apertures or ports in the cup wall that permit air to escape from the cup interior as the cup is filled with the impression paste and at the same time permit some of the paste to extrude through the ports. The latter expedient provides a convenient means for anchoring the formed cervical impression to the tray for easy removal from the cervix together with the tray as the tray is lifted away.

The hollow elongated stem should be of a length to facilitate removal of the vaginal speculum while the impression tray is held in place. The distal end of the stem can be provided with mounting notches and marking indicia for indicating a preselected orientation of the cup.

The paste dispensing syringe has a hollow body portion for containing the impression paste, a cannula or nozzle which fits into the hollow elongated stem and a movable, finger-actuated reciprocating plunger for dispensing the impression paste through the nozzle into the hollow elongated stem. Preferably, the nozzle is long enough to extend through the stem into the interior of the cup, is provided with a directional port, and is rotatable so as to facilitate a uniform distribution of the impression paste over the cervix uteri while the latter is enveloped by the cup. The distal end or tip of the nozzle extends into the cup when the syringe is received in the tray and preferably is offset with respect to the longitudinal axis of the nozzle. In a more preferred embodiment, the discharge port at the tip of the nozzle lies in a plane which intersects the longitudinal axis of the nozzle at an acute angle, preferably about 45 degrees.

To make an impression of the cervix, a vaginal speculum is inserted in the patient, the impression tray is passed thru the speculum and is positioned over the cervix with the stem protruding from the vagina. The impression paste is dispensed from the nozzle of the syringe after the nozzle is inserted into the stem and cup. The paste is distributed over the cervix and within the confines of the hollow cup of the tray. Preferably, the cup is transparent so as to permit observation of the paste distribution over the cervix. The speculum is then promptly removed, and the dispensed paste is permitted to harden in situ. Thereafter the tray, containing the fixed cervical impression, is removed from the vagina.

A more detailed explanation of the invention is provided in the following description and appended claims taken in conjunction with the accompanying drawings.

DESCRIPTION OF PREFERRED EMBODIMENTS

Figure 1:
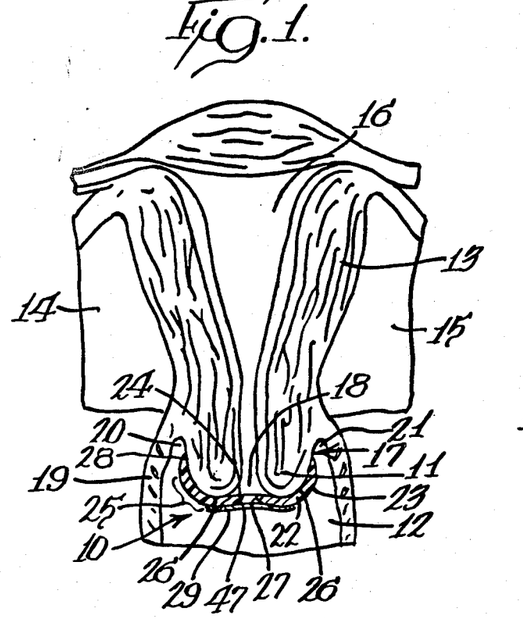
FIG. 1 is an elevational view, partly in section, of a portion of the internal organs of the female reproductive system with a cervical cap in place.

Referring to FIG. 1, valved cervical cap 10 is shown positioned on exocervical surface 17 of cervix uteri 11, i.e., on the portio vaginalis cervicis or that portion of uterus 13 that protrudes into vagina 12. Uterus 13 is supported by broad ligaments 14 and 15, and defines fundus 16 that terminates in cervical os 18. Vaginal wall 19 and cervix 11 together define the fornices vaginae, i.e., lateral fornices 20 and 21 as well as the anterior and posterior fornices (not shown).

Cap 10 is a cup-shaped elastomeric shell 22 having convex outer surface 23 and concave inner surface 24. Surface 26 of the portio vaginalis cervicis is not distorted by cap 10 and is in mating contact with at least a major portion of concave inner surface 24 and preferably along band 25 of shell 22 which is of substantially uniform rigidity. In the area of contact, concave inner surface 24 is substantially complementary with the contiguous surface 26 of the portio vaginalis cervicis. Preferably the thickness of shell 22 is substantially uniform, at least along peripheral band 25, for optimum stability of cap 10 when in place. Also, it is preferred that the band of substantially uniform thickness constitutes a major portion of shell 22.

Aperture 27 is provided in elastomeric shell 22 at the apex thereof and, as shown in FIG. 1, is positioned adjacent to cervical os 18 when cap 10 is in place. An external cover for aperture 27 is provided by elastomeric web 29 that is integral with shell 22. Web 29 is secured to shell 22 about a major portion of its periphery but also has an unsecured or free edge portion (FIG. 2) that together with adjacent surface portion of convex surface 23 defines a discharge port or external opening 43. Web 29 lies against shell 22 and substantially conforms to the contour thereof. In some instances web 29 may also be under tension and/or biased against convex surface 23. Web 29 and the covered portion of outer surface 23 together define a tunnel, channel, pocket or like passageway that communicates with aperture 27 but also forms a one-way valve. The passageway from aperture 27, between web 29 and surface 23, defines discharge port 43 away from the apex of shell 22, and thus spaced from aperture 27. Preferably the defined discharge port is situated at least about one aperture diameter away from aperture 27, and more preferably, is situated near or at shell periphery 35.

The positive one-way valve opens under minimal predetermined pressure applied from within the cap and permits the passage of fluids such as mucus, menstrual flow, and the like from fundus 16 to vagina 12 without disturbing the positioning of cervical cap 10 and without permitting the entry of sperm into fundus 16. Additionally, the precise fit of cervical cap 10 onto the portio permits mucus to flow around it; however, at the same time the forces generated by the flow of mucus assist in orienting and in holding cap 10 firmly in place and without exerting pressure on ther cervix itself unless an external displacing force is applied.

Figure 2:
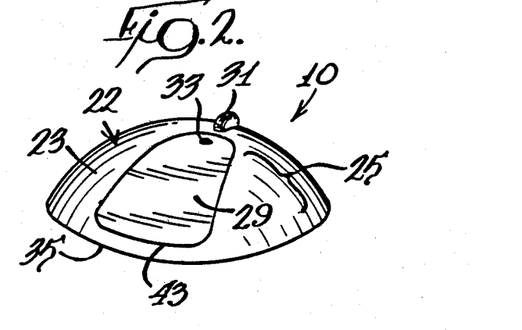
FIG. 2 is an enlarged perspective view of the cervical cap.

As shown in FIG. 2, optionally cap 10 can be provided with an integral tactile orientation marker 31 for the purpose of facilitating orientation of cap 27 upon insertion, as well as enabling the wearer to periodically assure herself that cap 10 remains properly positioned. Visual indicia 33 may also be provided on elastomeric web 29 in some instances for the purpose of facilitating the locating of aperture 27 underneath web 29 during manufacture of cap 10 as will be described in detail hereinbelow.

Shell 22 is dimensioned so as to have a depth sufficient to receive a major portion of the portio as illustrated in FIG. 1; however, periphery 35 of shell 22 usually terminates short of the fornices vaginae so as to guard against dislodgement of cap 10 during activity that may cause uterus 13 to shift position and/or to deform or distend the normal configuration of the fornices. To avoid dislodgment of the cap during momentary, severe uterine displacement it is important that peripheral edge 35 is sufficiently elastic to remain in contact with the exocervical surface contiguous therewith even during such momentary uterine displacement. For this purpose it is preferable that peripheral edge 35 be feathered, i.e., tapered or beveled as shown in FIG. 1 at 28.

Cap 10 preferably is positioned on cervix uteri 11 so that discharge port or external opening 43 of the valve defined by web 29 in conjunction with convex outer surface 23 is located in or near the posterior fornix and also at a location on surface 23 that is closer to shell periphery 35 than to the apex of the shell. In the embodiment illustrated in FIG. 2 discharge port 43 is substantially coincidental with periphery 35 and preferably is situated no more than about 1 to about 3 millimeters from periphery 35. This results in a manifold increase in the distance that sperm must travel to reach cervical os 18.

A portion of the increased distance for sperm travel is in vagina 12 where the environment is very inhospitable to sperm motility due to the relatively low ambient pH. Usually sperm can survive in the vaginal vault only for a time period of about one to two hours. Inasmuch as sperm can move at a velocity of about one or two millimeters per minute, the substantial increase in the distance that sperm must travel with cap 10 in place alone markedly reduces the likelihood of fertilization. Sperm travel to cervical os 18 via the valve means in cap 10 is possible only in close proximity to the walls defining the valve means. At least shell 22, and preferably both shell 22 and web 29 are of a thermoplastic elastomeric material. Such materials exhibit an inhibitory effect on sperm motility and are believed to disorient the cervical mucus, thus the likelihood of sperm reaching cervix uteri 11 is further reduced.

Shell 22 can be made of a wide variety of thermoplastic elastomeric materials, the so-called thermoplastic elastomers, such as polyolefin blends, styrene/elastomer block copolymers, copolyesters, and polyurethane block copolymers. While these thermoplastic elastomers differ chemically, their morphology is similar. Blocks or domains of relatively hard thermoplastic constituents link elastomeric constituents in a network that behaves like a chemically crosslinked rubbery structure. At forming temperatures the relatively hard thermoplastic domains of the structure soften and allow the polymeric material to flow. Upon cooling, these relatively hard domains resolidify and re-establish the rubber-like, elastic structure.

Thermoplastic elastomers that exhibit a surface charge provide a further advantage for the present purposes in that the presence of such a charge on the fabricated shell and/or web tends to inhibit sperm motility.

For purposes of the present invention, the shell materials particularly suitable are the styrene/elastomer block copolymers such as those commercially available from the Shell Chemical Company, Oak Brook, Ill., under the designation "Kraton" and "Kraton G" and described in U.S. Pat. No. 3,231,635 to Holden et al. These styrenic thermoplastic elastomers are block copolymers of polystyrene and an elastomer such as polyisoprene, polybutadiene, ethylene-propylene, or ethylene-butylene rubber.

While thermoplastic elastomeric materials of varying hardness may be used to fabricate shell 22, for optimum stability against dislodgment preferably the material should be harder than the cervical tissue that comes in contact therewith, yet the hardness should not be so high as to cause discomfort to the wearer or her consort. Preferably the shell material has a Shore A durometer hardness value of about 35 to about 70, and more preferably of about 45 to about 60.

The shell material can be opaque, semi-transparent or transparent; however, for ease of handling or positioning during fabrication of the cervical cap a transparent or clear material is preferred for the web at least in the region of the internal aperture of the shell to permit a visual alignment of the aperture with the cervical os region 81 (FIG. 7) of replica 80.

Web 29 can be unitary with shell 22 or integrally bonded thereto and thus integral with shell 22. Web 29 can be made from the same elastomeric material or from a different elastomeric material, as long as web 29 can be secured to shell 22. For ease of manufacture it is preferred to have web 29 of the same elastomeric material as the shell material but thinner. The shell-to-web thickness ratio usually is about 7:1 to about 3:1 and preferably about 5:1. In a typical cervical cap the shell thickness is about 1.5 millimeters and the web thickness is about 0.1 to about 0.4 millimeters.

The relative thicknesses of the shell and the web unitary or integral therewith in each instance depend on a variety of factors such as the manufacturing procedure, forming temperatures, modulus of elasticity, and the like considerations. In general, however, the web thickness is selected so as to provide a minimal valve-opening pressure, usually about 5 millimeters of mercury, or less, for the one-way valve formed by the coaction of web 29 with the outer surface 23 of shell 22 contiguous therewith.

The material for web 29 need not be thermoplastic as long as it exhibits the desired elasticity and can be secured to shell 22. Not only heat sealing or ultrasonic bonding but other bonding means, e.g., adhesive bonding, can be utilized. In addition to the aforementioned thermoplastic elastomers, the web portion of the present valved cervical cap can be made from materials such as natural rubber, silicone rubber, polyurethanes, fluorocarbon rubbers, styrene-butadiene rubbers, and the like.

Figure 3:
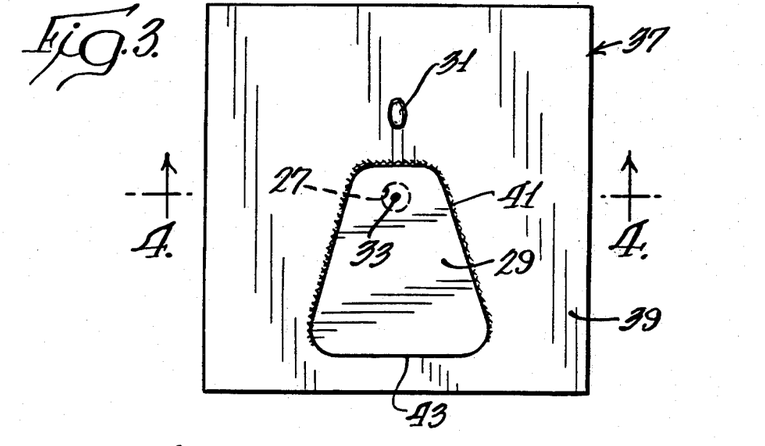
FIG. 3 is a plan view of a blank suitable for fabricating the cervical cap.
Figure 4A:
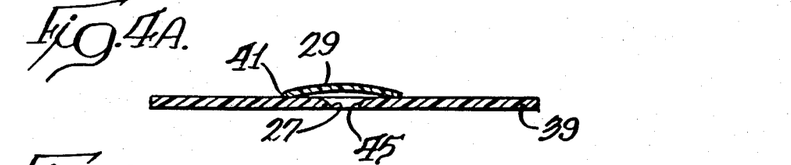
FIG. 4A is a sectional view taken along plane 4—4 in FIG. 3.

Valved cervical cap 10 can be fabricated by molding a blank of the type shown in FIGS. 3 and 4A wherein blank 37 comprises substantially planar sheet 39 of elastomeric material. Aperture 27 in the central region of sheet 39 is covered by elastomeric web 29. The contour of web 29 is not critical and can be generally fan-like, bell-shaped, trapezoidal, or circular, for example, as long as the web substantially conforms to the molded shell after the cap has been fabricated.

Web 29, in turn, is secured to sheet 39, e.g., by bonding peripheral region 41 thereof. The securement of web 29 to sheet 39, and thus ultimately to cap 10, is sufficient to permanently attach web 29 to sheet 39 but provides an unsealed, i.e., free, edge portion which serves to define, in part, external valve opening or discharge port 43. In essence, web 29, when secured to sheet 39, defines a pocket or pockets communicating with underlying aperture 27 and provides a one-way passageway or channel between web 29 and that portion of sheet 39 which ultimately becomes a web-covered portion of the convex outer surface 23 for cap 10, terminating in discharge port 43 that is situated at least one aperture diameter away from aperture 27. Preferably the cross-sectional area of the defined channel or passageway increases with increasing distance from aperture 27 as measured along convex surface 23 of shell 22. Thus, in case of a trapezoidal web, for instance as shown in FIG. 3, the relatively shorter of the two substantially parallel sides of the trapezoid is positioned nearer to aperture 27 than the relatively longer parallel side, and bonded peripheral region 41 extends about the major portion of the periphery of aperture 27. The diameter of aperture 27 is usually about 5 to about 10 millimeters.

Aperture 27 can be a through-aperture with rectangular edges, if desired. However, during fabrication, the relatively thin, thermoplastic, elastomeric web may be drawn or forced into aperture 27 too far and, by such stretching, may be excessively deformed or even perforated at the line of contact with a rectangular, sharp edge defining aperture 27. The use of such relatively thin webs, if desired, is facilitated if the aperture-defining edge portion adjacent to web 29 is beveled as at 45 in FIG. 4A or rounded as at 47 in FIG. 1. In this manner the likelihood that web 29 may be perforated or unduly distorted during fabrication is reduced. Tactile orientation marker 31 is positioned adjacent to a sealed juncture of web 29 and sheet 39.

Figure 4B:
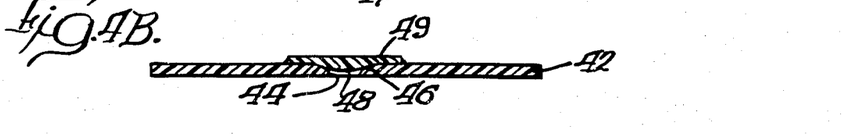
FIG. 4B is a sectional view similar to that in FIG. 4A but showing an alternate cross-sectional configuration for the valve means of the cervical cap.

An alternate, suitable one-way valve configuration utilizing a relatively thin web is illustrated in FIG. 4B where aperture 44 in thermoplastic elastomeric sheet 42 is covered by web 49 having unitary protuberance 48 extending into aperture 44 and contacting beveled surface 46, i.e., the web 49 is thicker in the region of aperture 44. When a custom, valved cervical cap is fabricated using a cap blank of the type shown in FIG. 4B, protuberance 48 will abut beveled surface 46 and thus will prevent excessive deformation of the web itself during fabrication.

Figure 8:
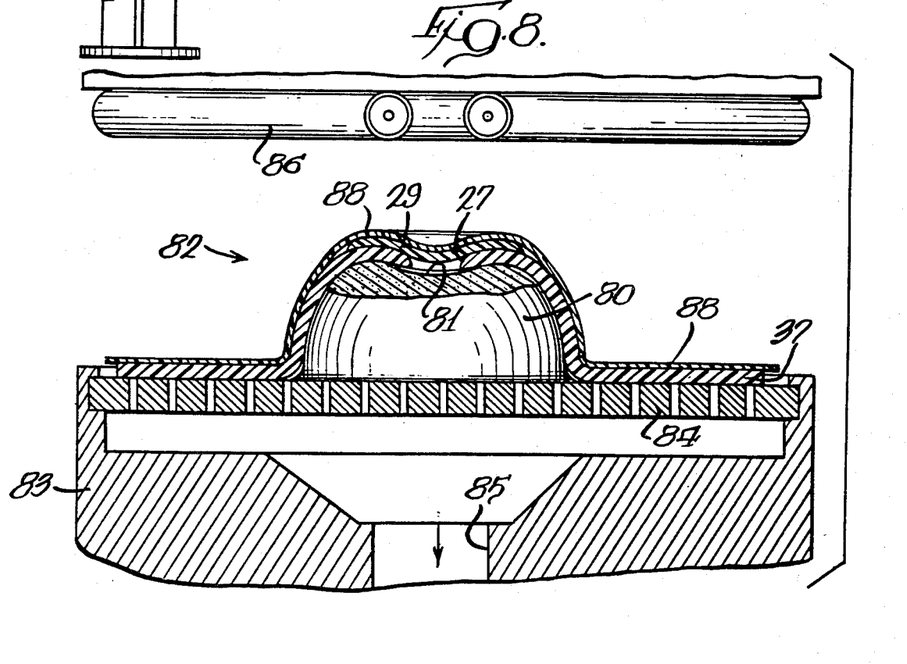
FIG. 8 is an enlarged sectional elevational view of a vacuum molding apparatus for molding a cervical cap.

It should be noted, however, that even in the case of a substantially uniformly thick web some deformation into the shell aperture, such as aperture 27 (FIGS. 1, 3 and 8), is not objectionable as long as web integrity is not impaired. Such deformation, as best seen in FIG. 8, also can provide a unitary protuberance that projects into the aperture and enhances the valving action. In addition, the web may be relatively thicker in the region overlying the aperture.

In some instances, particularly when sheet 39 is relatively thick, e.g., of the order of about 2.5 millimeters or more, it is desirable to extend bevel 45 on the aperture edge portion substantially to the juncture 41 of sheet 39 and web 29 so as to provide a substantially uniform thickness throughout. Alternatively, or in addition, the region surrounding aperture 27 and covered by web 29, in the region between juncture 41 and aperture 27 may be countersunk or thinned out for the same purpose.

A prefabricated blank of the type described offers the substantial advantages of ease of custom cap fabrication by a practitioner associated with the practicing physician or with a medical laboratory and utilizing the implement of the present invention.

For optimum fit, concave inner surface 24 of cap 22 is substantially complementary with the surface of the portio vaginalis cervicis contiguous therewith. While it is desirable that concave inner surface 24 projects slightly toward cervical os 18 about the periphery of aperture 27, i.e., has local convexity in the aperture region complementary to the concavity of the cervix in the region surrounding cervical os 18, no portion of surface 24 enters cervical os 18. To this end, the cervix in its normal, undistorted configuration is first replicated as a rigid mold, e.g., in plaster, and the obtained replica is then utilized to mold the cervical cap.

Initially an impression of cervix uteri is made using a physiologically tolerable, hardenable paste. Suitable for this purpose is an aqueous paste made from dental impression powder, e.g., using an algin derivative, usually an alginate such as sodium alginate.

Figure 5:
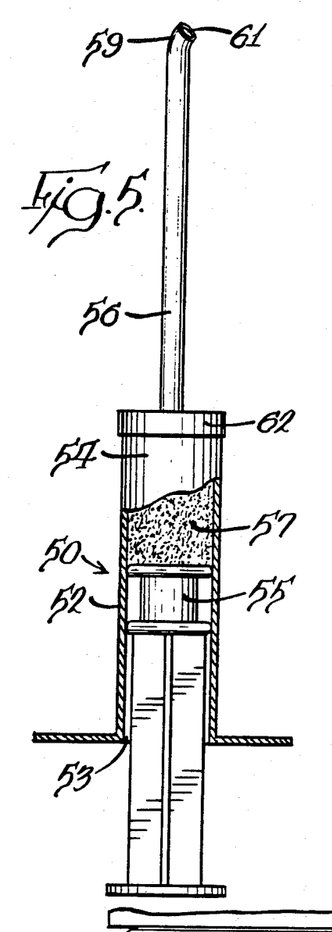
FIG. 5 is a perspective view, shown partly in cross-section, of an impression paste dispensing syringe that can be used with the implement embodying the present invention.
Figures 6, 7:
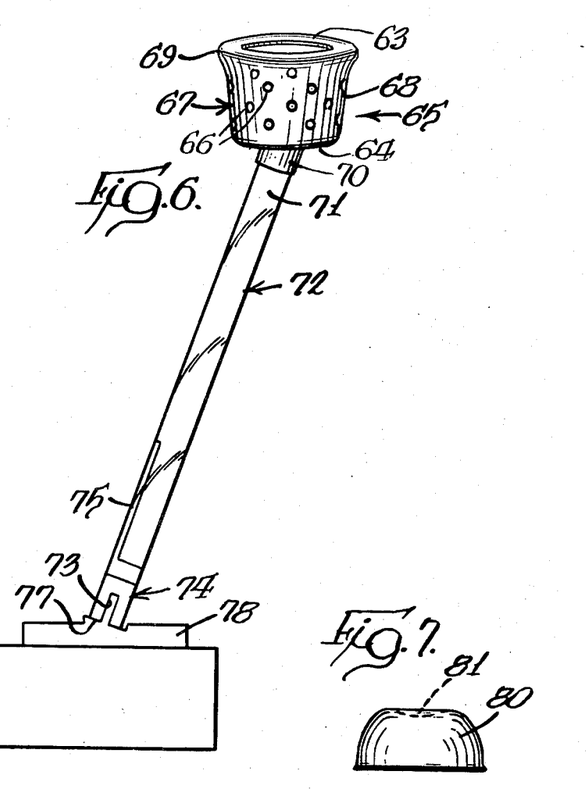
FIG. 6 is a perspective view of an impression tray embodying the present invention.
FIG. 7 is a side elevational view showing a cast replica of the cervix of female uterus that can be made utilizing the present impression tray.

The cervical impression is obtained utilizing the implements shown in FIGS. 5 and 6. Syringe 50, shown in FIG. 5, includes hollow body portion 52 having an open end 53 and opposed dispensing end 54 that terminates into elongated nozzle 56 in communication with hollow body portion 52. Plunger 55 is positioned within hollow body portion 52 and is adapted to dispense the syringe contents through nozzle 56. Impression paste 57, e.g., aqueous alginate paste, is contained within hollow body portion 52. To facilitate the distribution of impression paste 57 over the cervix during the course of making the impression, it is preferable to have a nozzle the distal end 59 of which is offset from the longitudinal axis of the nozzle itself. In this manner nozzle discharge port 61 is situated in a plane that is at an acute angle, preferably at an angle of about 45 degrees, with respect to the longitudinal axis of nozzle 56, and can dispense impression paste 57 laterally over the cervix in all directions by simply rotating syringe 50. In an alternate manner, nozzle 56 can be rotatably mounted on syringe body 52 by means of nozzle-bearing hub 62 that is rotatable with respect to syringe body 52.

Preparatory to making a cervical impression as contemplated by the present invention, vagina 12 is expanded using a vaginal speculum so as to expose the cervix. Thereafter impression tray 65 (FIG. 6) is inserted through the speculum and into the vagina, and positioned so that hollow cup 67 thereof envelops the cervix. Cup 67 has a flexible, preferably transparent, side wall 68 and annular bottom 64, both made from an elastomeric material such as silicone rubber, polyurethane, or the like, that terminates in a rim defining the open end of the cup and preferably including a peripheral, outwardly bulging, anterior lip 69 the purpose of which is to keep out adjacent vaginal wall. Circumferential flange 63 is flexible and resilient, and extends radially inwardly from the annular rim of cup 67. Wall 68, lip 69, and inwardly extending flange 63 are designed so as to trap the cervix and to prevent its upward rotation with attendant closure of the anterior fornix space when the patient is in a supine position while the cervical impression is made. Additionally, the flange also provides a retainer means forming a resilient seal against the exocervical surface of the cervix and aids the retention of the dispensed impression paste in the cup during molding.

The width of flange 63 is substantially less than the radius of the mouth or opening defined by the rim of cup 67. The flange width can be about 1/10 to about ¼ of the rim aperture radius. A flange width of about 1/6 to about 1/7 of the rim aperture radius is preferred. When the cup has a substantially bell-like configuration with an outwardly flared mouth, preferably the flange extends inwardly from the rim defining the mouth at least for a distance that is substantially the same as the outwardly flare of the rim.

Thickness of flange 63 can be the same as that of wall 68, but preferably is less than the thickness of wall 68, usually at least about 20 percent less. More preferably, flange 63 is about 0.8 to about 1.2 millimeters thick. The thickness of wall 68 usually is about 1 to about 1.6 millimeters, depending on the thickness of the associated flange.

Flexible wall 68 is further provided with a plurality of spaced perforations such as perforation 66. At the bottom thereof cup 67 is provided with a cup access aperture surrounded by downwardly depending sleeve 70 which can be made of the same material as wall 68. Proximal end 71 of a hollow, elongated stem or tube 72 is received within sleeve 70. Stem 72 defines a passageway that communicates with the interior of cup 67 through the cup access aperture. A pair of opposed mounting notches, such as notch 73, are provided in distal end 74 of stem 72, to prevent rotation of the stem during the casting of a cervical replica as will be discussed in greater detail hereinbelow. While a pair of notches is shown in the drawing, a single notch can also be used. Alternatively, friction fit can be provided between stem 72 and the stem mounting means on vibrating table 78. Also at or near distal end 74 marker means 75 is provided on stem 72 for indicating a preselected orientation of cup 67.

While cup 67 and stem 72 can be coaxial, for ease of manipulation and insertion during the making of a cervical impression, and also to facilitate the entrapment of the cervix, it is preferred that the longitudinal axes of cup 67 and stem 72 intersect at an included angle of about 15 to about 25 degrees, and more preferably about 20 degrees.

To make a cervical impression once tray 65 is appropriately positioned enveloping the cervix, nozzle 56 is inserted through hollow stem 72. Preferably, length of nozzle 66 is selected so as to extend for substantially the length of stem 72. More preferably distal end 59 projects into cup 67 through the bottom aperture thereof but remains spaced from the cervix. Hub 62 (FIG. 5) on the syringe, upon abutting open end 77 of stem 72, provides a positive stop that prevents nozzle aperture 61 from coming in contact with the cervix. In instances where nozzle 56 is longer than stem 72, appropriate stop means can be provided on nozzle 56 itself or within stem 72 at the proximal end 71 received within sleeve 70.

Impression paste 57 is then dispensed from syringe 50 and distributed so as to cover the cervix, speculum is removed from the vagina without removing tray 65, and the paste permitted to set. The speculum, when in position, pulls on the ligaments supporting the uterus and cervix and thus distorts the cervix uteri. Therefore, it is important to remove the speculum from the vagina or at least to close the speculum blades so as to permit the cervix to return to its normal, undistorted configuration before the impression paste has set.

The length of stem 72 is selected long enough to permit the easy removal of the speculum without disturbing the position of tray 65. As the impression paste fills cup 67, minor amounts of the paste exude through perforations 66 and, upon setting, anchor the formed impression within tray 65.

After the paste has set, usually within about 90 seconds, tray 65 together with the cervical impression contained therewithin is lifted from the cervix and placed onto vibrating table 78 for casting a replica of the cervix.

The casting operation entails pouring a slurry of plaster of Paris, or like casting material, into tray 65 while the latter is vibrated to permit any trapped air to rise to the surface and to assure that each and every crevice of the formed impression is filled with the slurry. After the slurry has hardened, replica 80 (FIG. 7) is removed from tray 65 and is ready for use in fabricating cervical cap 10.

To this end vacuum molding techniques, e.g., drape forming, can be readily utilized; however, any other molding technique can be utilized as long as the material to be molded can be made to conform closely to the cervical replica, for example, by means of positive air pressure. For purposes of illustration a preferred vacuum molding technique will be described in detail hereinbelow.

Referring to FIG. 8, vacuum molding apparatus 82 comprises base 83 that supports foraminous plate 84 and heat source 86, e.g., a calrod heating element or infrared lamp, in a spaced relationship relative to plate 84. Alternatively, heat can be supplied by a stream of hot air. In the case of a radiant heat source, such as an infrared lamp, the heat-radiating surfaces can be contoured so as to provide a substantially uniform distance between the heat source and the blank portion nearest thereto. Channel 85 in base 83 communicates with a vacuum source (not shown) and permits vacuum to be drawn through plate 84.

Replica 80 is positioned on plate 84 and blank 37 is positioned thereover so that visual indicia 33 is superposed over cervical os region 81 of replica 80. A release agent, e.g., an aerosol spray of lecithin commercially available under the designation "Pam" from Boyle-Midway, Inc., New York, N.Y. 10017, is applied to the exposed surface of blank 37, and between the web and the underlying sheet. The blank is then covered with thin protective sheet 88, e.g., a polyethylene terephthalate film, or the like. Heat source 85 is then turned on and heat applied to sheet 37 until it begins to soften and conform to replica 80 by its own weight. Thereafter the vacuum source is turned on and vacuum is drawn through foraminous plate 84 so as to press softened sheet firmly against replica 80. Alternatively, instead of vacuum forming, the cap can be made by applying a superatmospheric pressure to a blank positioned over the replica. Heat source 86 is then turned off or removed, and the formed sheet is permitted to cool while vacuum or positive pressure is maintained. Once cooled and set to a permanent contour, sheet 37 is removed from replica 80, and the formed cervical cap is trimmed to the desired shell depth. The specific shell depth in each instance will depend on the contour of the portio vaginalis cervicis in a given case; however, the shell peripheral edge, i.e., periphery 35, should not extend into the fornices vaginae. The feathering or beveling of shell periphery 35 is usually done during the final trimming operation.

Valved cervical caps embodying the present invention, made from styrene/elastomer block copolymers, and having the general configuration shown in FIG. 2 have been satisfactorily worn by sexually-active female volunteers for a cumulative time period in excess of 290 months.

Figure 9:
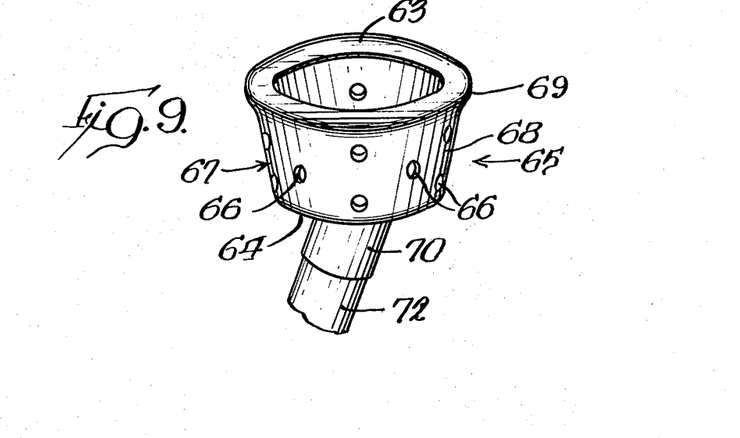
FIG. 9 is an enlarged fragmentary perspective view of the impression tray shown in FIG. 6.
Figure 10:
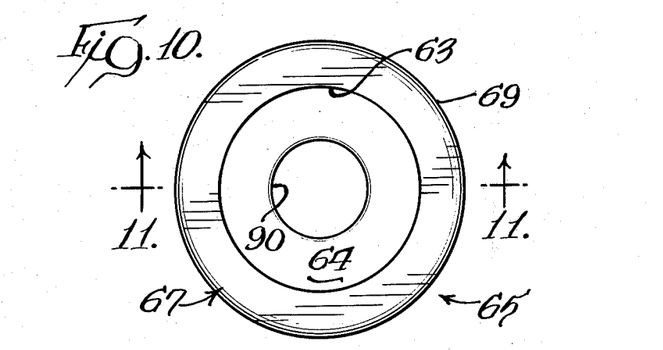
FIG. 10 is a top plan view of the impression tray shown in FIG. 9.
Figure 11:
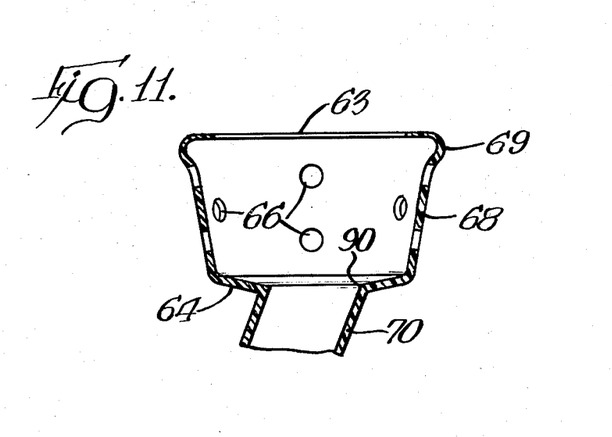
FIG. 11 is a cross-sectional view of the impression tray of FIG. 9 taken substantially along plane 11—11 in FIG. 10.

Enlarged views of impression tray 65 are shown in FIGS. 9-11. Flexible, resilient circumferential flange or retainer 63 is unitary with cup 67 and extends radially inwardly from the bulging annular lip 69 defining the outwardly flared rim of bell-shaped hollow cup 67. The inside diameter of flange 63 defines the nominal working diameter for the hollow cup. Flange 63 also serves as a retainer and seal to resiliently and sealingly engage and firmly cushion cup 67 against the exocervical surface of the cervix uteri so as to facilitate retention of the dispensed impression paste within cup 67 during in situ molding of the cervical impression, i.e. to substantially prevent the impression paste from leaking out of the open end (mouth) of cup 67.

In a typical example, impression tray 65 has a cup provided with flange 63 having an inside diameter of about 35 millimeters and an outside diameter of about 41 millimeters so that the flange or retainer extends radially inwardly about 3 millimeters from the rim. The cup wall thickness is about 1.3 millimeters, and the flange thickness is about 1.1 millimeters. In another example, the cup flange has an inside diameter of about 40 millimeters and an outside diameter of about 46 millimeters, with the flange or retainer again extending radially inwardly about 3 millimeters from the rim. In this particular example, the cup wall thickness is about 1.3 millimeters, and the flange thickness is about 1 millimeter.

Preferably, flange 63 is made out of the same transparent medical grade material as cup 67; however flange 63 can be made out of a different material or have different physical properties in those circumstances where different physical properties would be desirable.

The array of perforations or apertures 66 in wall 68 provides air passageways and permits minor amounts of impression paste to exude through the apertures to the exterior surface of the wall 68 during molding. Upon setting, these minor amounts of paste interlockingly anchor the formed cervical impression against the wall of the cup. Wall 68 need not have perforations if the impression paste, when set, will sufficiently adhere to the cup's wall or will otherwise be retained within the cup while the tray is removed from the patient.

Sleeve 70 is integral with cup 67, extends downwardly from annular concave bottom wall 64 of cup 67, and fits upon hollow stem 72. Annular bottom wall 64 defines cup access aperture 90 which provides an inlet for ingress of the impression paste into cup 67.

The foregoing disclosure and the accompanying drawings are intended as illustrative and are not to be construed as limiting. Still other variations within the spirit and scope of the present invention as defined by the claims are possible and will readily present themselves to those skilled in the art.

I claim:

1. An in situ uteri impression-molding implement comprising:
   a cervix uteri-receiving cup having a flexible side wall terminating in a rim, a bottom defining a cup access aperture, and a resilient circumferential flange extending inwardly from the rim; and
   an elongated hollow stem at the bottom of the cup and providing a passageway communicating with the cup interior through the cup access aperture, the passageway being adapted to receive an elongated nozzle inserted therein after the circumferential flange is positioned on the exocervical surface of the cervix uteri, and a hardenable paste which is introduced by the nozzle through the passageway and into the cup to prepare an impression of the cervix uteri.

2. The implement in accordance with claim 1 further including a sleeve joined to the bottom at the exterior surface thereof and surrounding the cup access aperture, and wherein the hollow stem is received within the sleeve.

3. The implement in accordance with claim 1 wherein the rim includes an outwardly bulging lip and wherein the flange extends inwardly from the lip.

4. The implement in accordance with claim 1 wherein the rim terminates in a circumferential flange having a thickness that is less than the thickness of the flexible side wall.

5. The implement in accordance with claim 1 wherein the flange has a thickness of about 0.8 to about 1.2 millimeters.

6. The implement in accordance with claim 1 wherein the width of the flange is about 1/10 to about ¼ of the radius of the cup opening defined by the rim.

7. The implement in accordance with claim 1 wherein the width of the flange is about 1/6 to about 1/7 of the radius of the cup opening defined by the rim.

8. The implement in accordance with claim 1 wherein the flexible side wall is provided with a plurality of perforations spaced from one another.

9. The implement in accordance with claim 1 wherein the longitudinal axes of the cup and the stem intersect at an included angle of about 15 to about 25 degrees.

10. The implement in accordance with claim 1 wherein the longitudinal axes of the cup and the stem intersect at an included angle of about 20 degrees.

11. The implement in accordance with claim 1 wherein the distal end of the stem is provided with a mounting notch and wherein marker means are provided on the stem indicating a preselected orientation of the cup.

12. The implement in accordance with claim 1 wherein the cervix uteri-receiving cup has substantially the configuration of a bell and wherein the flange extends inwardly a distance that is substantially the same as the outwardly flare of the rim defining the mouth of the cup.

13. The implement in accordance with claim 1 wherein the thickness of the flange is at least about 20 percent less than the thickness of the side wall.

* * * * *